US012605752B2

(12) United States Patent
D'Alessio et al.

(10) Patent No.: US 12,605,752 B2
(45) Date of Patent: Apr. 21, 2026

(54) METHOD FOR SEPARATING AND RECOVERING SUPER-ABSORBENT POLYMERS (SAP) FROM POST-CONSUMER ABSORBENT SANITARY PRODUCTS

(71) Applicant: The Procter & Gamble Company, Cincinnati, OH (US)

(72) Inventors: Nicola D'Alessio, Spoltore (IT); Tonino Caruso, Spoltore (IT)

(73) Assignee: The Procter & Gamble Company, Cincinnati, OH (US)

( * ) Notice: Subject to any disclaimer, the term of this patent is extended or adjusted under 35 U.S.C. 154(b) by 851 days.

(21) Appl. No.: 17/781,769

(22) PCT Filed: Nov. 27, 2020

(86) PCT No.: PCT/IB2020/061207
§ 371 (c)(1),
(2) Date: Jun. 2, 2022

(87) PCT Pub. No.: WO2021/130575
PCT Pub. Date: Jul. 1, 2021

(65) Prior Publication Data
US 2023/0339004 A1 Oct. 26, 2023

(30) Foreign Application Priority Data

Dec. 24, 2019 (IT) ........................ 102019000025570

(51) Int. Cl.
*B09B 3/70* (2022.01)
*A61L 11/00* (2006.01)
(Continued)

(52) U.S. Cl.
CPC ................ *B09B 3/70* (2022.01); *A61L 11/00* (2013.01); *B09B 3/35* (2022.01); *B09B 3/40* (2022.01);
(Continued)

(58) Field of Classification Search
CPC ..... B09B 3/70; B09B 3/40; B09B 3/35; C08J 11/08; C08J 11/16; B29B 17/02; B29B 17/0412; A61L 11/00
See application file for complete search history.

(56) References Cited

U.S. PATENT DOCUMENTS

2018/0272395 A1* 9/2018 Herriott .................... B09B 3/35
2019/0224886 A1* 7/2019 Somma ................... B02C 19/06
2020/0016794 A1* 1/2020 Konishi ................. A61L 11/00

FOREIGN PATENT DOCUMENTS

CN 109232819 A 1/2019
JP H04317785 A 11/1992
(Continued)

OTHER PUBLICATIONS

Machine translation of JP H06313008 by Yamamoto et al. (Year: 1994).*
(Continued)

*Primary Examiner* — Christina H.W. Rosebach
(74) *Attorney, Agent, or Firm* — Anna E. Haller

(57) ABSTRACT

A method for separating a fraction of super-absorbent polymers (SAP) from post-consumer absorbent sanitary products, said post-consumer absorbent sanitary products further including at least one cellulose fraction and one plastic fraction. The method includes the steps of sterilizing the post-consumer absorbent sanitary products and treating said post-consumer absorbent sanitary products by immersion in a bath with an aqueous solution containing at least one oxidizing compound. The oxidizing compound is preferably selected from the group consisting of sodium persulfate, potassium persulfate, ammonium persulfate, potassium monopersulfate, and hydrogen peroxide; preferably hydrogen peroxide. The treatment by immersion allows cross-link cleavage and solubilizing of the SAP contained in said post-consumer absorbent sanitary products, and obtaining a
(Continued)

suspension comprising i) a solid fraction and ii) a liquid fraction, wherein the liquid fraction comprises linear polyacrylate derived from the cross-link cleavage and solubilization of SAP.

11 Claims, 6 Drawing Sheets

(51) Int. Cl.

| | |
|---|---|
| *B09B 3/35* | (2022.01) |
| *B09B 3/40* | (2022.01) |
| *B29B 17/02* | (2006.01) |
| *B29B 17/04* | (2006.01) |
| *C08J 11/08* | (2006.01) |
| *C08J 11/16* | (2006.01) |
| *B09B 101/67* | (2022.01) |
| *B29B 17/00* | (2006.01) |

(52) U.S. Cl.

CPC .......... *B29B 17/02* (2013.01); *B29B 17/0412* (2013.01); *C08J 11/08* (2013.01); *C08J 11/16* (2013.01); *B09B 2101/67* (2022.01); *B29B*

*2017/0015* (2013.01); *C08J 2301/02* (2013.01); *C08J 2333/04* (2013.01)

(56) References Cited

FOREIGN PATENT DOCUMENTS

| | | | | |
|---|---|---|---|---|
| JP | H06313008 | * 11/1994 | ................ | C08F 8/50 |
| JP | 2001316519 A | 11/2001 | | |
| JP | 2019131789 A | 8/2019 | | |
| WO | 2013044266 A1 | 3/2013 | | |
| WO | WO-2018060827 A1 * | 4/2018 | ......... | B29B 17/0412 |
| WO | WO-2018179617 A1 * | 10/2018 | ............. | B29B 17/02 |

OTHER PUBLICATIONS

PCT Search Report and Written Opinion for PCT/IB2020/061207 dated Feb. 11, 2021, 14 pages.

* cited by examiner

METHOD FOR SEPARATING AND RECOVERING SUPER-ABSORBENT POLYMERS (SAP) FROM POST-CONSUMER ABSORBENT SANITARY PRODUCTS

CROSS-REFERENCE TO RELATED APPLICATIONS

This application is a 371 National Stage of International Application No. PCT/IB2020/061207, filed Nov. 27, 2020, which claims priority to Italian Patent Application No. 102019000025570 filed Dec. 24, 2019. The disclosure of each of the above applications is incorporated herein by reference in its entirety.

FIELD OF THE INVENTION

The present description relates to recycling of post-consumer absorbent sanitary products. In particular, the present description relates to separation methods of post-consumer absorbent sanitary products into different components for successive re-use.

BACKGROUND OF THE INVENTION

Absorbent sanitary products are generally composed of different materials, including, for example, plastic film, cellulose fluff, and superabsorbent polymers (SAP). These sanitary products therefore contain valuable materials whose recovery for re-use on the market is a decidedly desirable goal.

Methods known to date for treating absorbent sanitary products in order to separate the different components may comprise steps wherein the cellulose fraction is separated from the super-absorbent polymers (SAP), for example, by vibration mechanical separation, by enzymatic action on the cellulose in combination with mechanical separation of the SAP deactivated with calcium chloride ($CaCl_2$)), or by extraction in the supercritical phase. There are also known methods for separating the plastic fraction from the SAP (previously deactivated with calcium or Al ions or the like) by means of combinations of enzymatic actions and physical separations.

Criticalities related to known methods for treating post-consumer absorbent sanitary products can derive from the difficulty of effectively separating the super-absorbent polymers (SAP) from the other components, for example, from the cellulose fraction and from the plastic fraction. Cellulose and plastic recovered from these post-consumer products can in fact include SAP residues in variable quantities capable of affecting the degree of purity of the separated components.

OBJECT AND SUMMARY OF THE INVENTION

The present description aims to provide a method for treating post-consumer absorbent sanitary products that allows obtainment of an effective separation of super-absorbent polymers (SAP) of the plastic and cellulose fractions while preserving the quality of the products for convenient reuse or recycling in the market.

According to the present description, this object is achieved thanks to a method having the characteristics forming the subject of the attached claims. The claims form an integral part of the disclosure provided here in relation to the described method.

The present description provides a method for separating the fraction of super-absorbent polymers (SAP) from post-consumer absorbent sanitary products, said post-consumer absorbent sanitary products further comprising at least one cellulose fraction and one plastic fraction, the method comprising at least the steps of:

sterilizing said post-consumer absorbent sanitary products to obtain sterilized material, treating said post-consumer absorbent sanitary products by immersion in a bath with an aqueous solution containing at least one oxidizing compound, preferably selected from the group consisting of sodium persulfate, potassium persulfate, ammonium persulfate, potassium monopersulfate, and hydrogen peroxide; preferably hydrogen peroxide, to cleave the cross-links and solubilize the SAP contained in said post-consumer absorbent sanitary products, obtaining a suspension that comprises i) a solid fraction and ii) a liquid fraction, said liquid fraction comprising non-cross-linked linear polyacrylate (LPA) derived from the cross-link cleavage and solubilization of the SAP.

The sterilization step may be carried out by heating the post-consumer absorbent sanitary products at a temperature between 120° C. and 140° C. and at a pressure between 1 bar and 3.6 bar; preferably, the sterilization step is carried out in an autoclave.

In one or more embodiments, the aqueous solution may comprise only hydrogen peroxide as the oxidizing compound. Furthermore, the step of treating by immersion can be advantageously carried out at a temperature between 65° C. and 100° C.

The method described here may further comprise a step of separating the solid phase from the liquid phase.

In one or more embodiments, the method may further comprise at least one washing step of the solid phase, said washing step preferably carried out with water.

In one or more embodiments, the method may comprise at least one step of purifying the liquid fraction containing linear polyacrylate (LPA) from any cellulose or plastic residues, preferably by means of filtration on disc filters.

The liquid phase, optionally purified, can be used for cross-linking methods of the linear polyacrylate (LPA) and consequent production, for example, of new SAP, as will be described by way of example below.

The solid fraction obtained from the described method, possibly subjected to at least one washing step, may comprise cellulose and plastic with a high degree of purity, in which the SAP content is less than 1% by weight (weight/weight). Purity and identity of the cellulose obtained from the method were determined and confirmed by analysis in Fourier transform infrared spectrophotometry, FTIR, combined with ATR-Attenuated Total Reflectance for analysis of the cellulose, American Journal of Analytical Chemistry, 2018, Vol. 9, pages 303-310. The purity and identity of the plastic obtained from the method were determined and confirmed by analysis in Fourier transform infrared spectrophotometry, FTIR, combined with the UNI EN ISO 6427/2013 and ISO 16152/2005 Methods.

BRIEF DESCRIPTION OF THE DRAWINGS

The method will now be described in detail with reference to the attached drawings, given purely by way of non-limiting example, wherein.

DETAILED DESCRIPTION

In the following description, numerous specific details are provided to allow a thorough understanding of embodiments. The embodiments can be put into practice without one or more of the specific details or with other methods, components, materials etc. In other cases, well-known structures, materials or operations are not shown or described in detail to avoid confusing aspects of the embodiments.

Reference throughout the present disclosure to "one embodiment" or "an embodiment" indicates that a particular aspect, structure or characteristic described with reference to the embodiment is included in at least one embodiment. Thus, forms of the expressions "in one embodiment" or "in an embodiment" at various points throughout the present description are not necessarily all referring to the same embodiment. Moreover, the particular aspects, structures or characteristics can be combined in any convenient way in one or more embodiments. The titles provided in this description are for convenience only and do not interpret the scope or object of the embodiments.

The expression "absorbent sanitary products" generally refers to disposable absorbent products, such as diapers for babies, incontinence pads for adults, sanitary towels, bed linings, etc. These absorbent products may comprise plastic, super-absorbent polymers, cellulose or even only plastic and super-absorbent polymers.

As anticipated in the preceding sections, methods are currently known for treating post-consumer absorbent sanitary products in order to obtain the separation of the various components, such as, for example, cellulose, plastic, and super-absorbent polymers (SAP).

Figure 1:
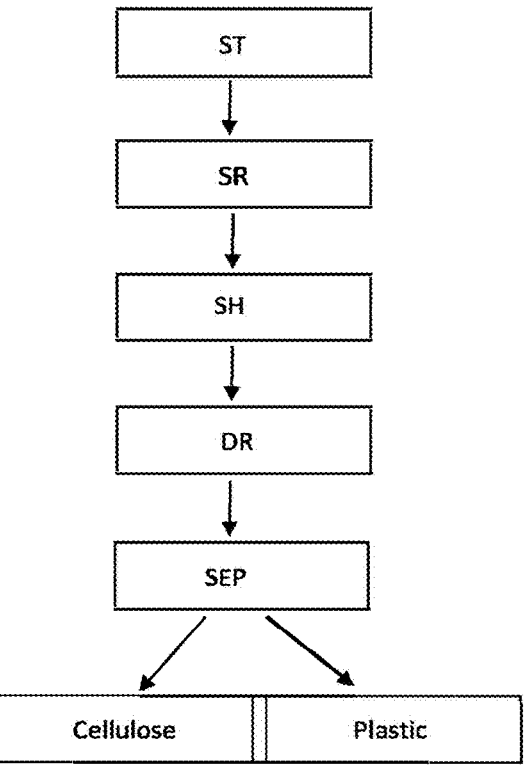
FIG. 1 represents a diagram of a known method for treating post-consumer absorbent sanitary products.

A method known to date for treating and separating the various components of post-consumer absorbent sanitary products may comprise the steps illustrated, for example, in FIG. 1 of the present application and described in document WO 2018/060827 by the same Applicant. This method may comprise the step of sterilizing SR the post-consumer absorbent sanitary products, shredding SH the sterilized products, drying DR the sterilized and shredded products, and separating SEP the sterilized, shredded and dried products into plastic and cellulose.

Criticalities related to methods for treating post-consumer absorbent sanitary products can derive from the difficulty of effectively separating the super-absorbent polymers (SAP) from the other components, for example, from the cellulose fraction and from the plastic fraction.

Cellulose and plastic recovered from post-consumer sanitary products can, in fact, include SAP residues in variable quantities, as described below.

The super-absorbent polymer is usually prepared by copolymerization of one or more monomers (acrylic acid, sodium or potassium acrylate or methacrylate, and/or acrylamide) from which the basic structure (backbone) of the material originates, i.e. a sodium linear polyacrylate, LPA (Spectra DataBase: Spectrum ID 8XQMEFCFImm, Copyright© 1980, 1981-2018 Bio-Rad Laboratories, Inc.). The use of bifunctional cross-linking agents (cross-linkers) (for example, N, N-methylene-bis-acrylamide (MBA), Ethylene glycol dimethacrylate (EGDMA), Diallyl phthalate (DP), or Triethylene glycol dimethacrylate (TEGDMA) results in a degree of cross-linking of the linear polyacrylate (LPA) that depends on the amount of cross-linking agent used. The result is the formation of a polymeric network which bears negatively charged carboxylate groups (—COO$^-$). Due to electrostatic repulsions, the network can expand locally providing spaces therein that can absorb (and retain) volumes of water or aqueous solutions. The cross-linking also renders the SAP polymer insoluble in an aqueous environment.

The inventors of the present application have identified specific operating conditions of a method that comprises a step of treating the post-consumer absorbent sanitary products by immersing them in a bath with an aqueous solution containing an oxidizing compound. The at least one oxidizing compound is preferably selected from the group consisting of sodium persulfate, potassium persulfate, ammonium persulfate, potassium monopersulfate, and hydrogen peroxide; preferably hydrogen peroxide. The aqueous solution may also comprise only hydrogen peroxide as the oxidizing compound.

This step allows a suspension to be obtained comprising i) a solid fraction comprising at least one of the cellulose and plastic fractions and ii) a liquid fraction comprising non-cross-linked linear polyacrylate (LPA) derived from the cross-link cleavage and solubilization of SAP. In particular, the liquid fraction comprises non-cross-linked linear polyacrylate in the form of sodium or potassium non-cross-linked linear polyacrylate (LPA).

The treatment step by immersion favors an effective cross-link cleavage, solubilization and separation of the SAP from the solid fraction that comprises plastic and cellulose.

In particular, the treatment step by immersion in the solution containing at least one oxidant determines the destructuring of the cross-links existing between the polymers constituting the SAP, freeing the basic structure or linear polyacrylate, LPA (here also defined as acrylate polymer in linear form) which passes into the liquid fraction.

The method described here also allows i) reducing until completely inhibiting the ability of the SAP to swell by absorbing water and ii) obtaining the total solubilization of the SAP as linear polyacrylate (LPA).

This linear polyacrylate (LPA) may then be advantageously subjected to cross-linking steps for producing, for example, new SAP.

Figure 3:
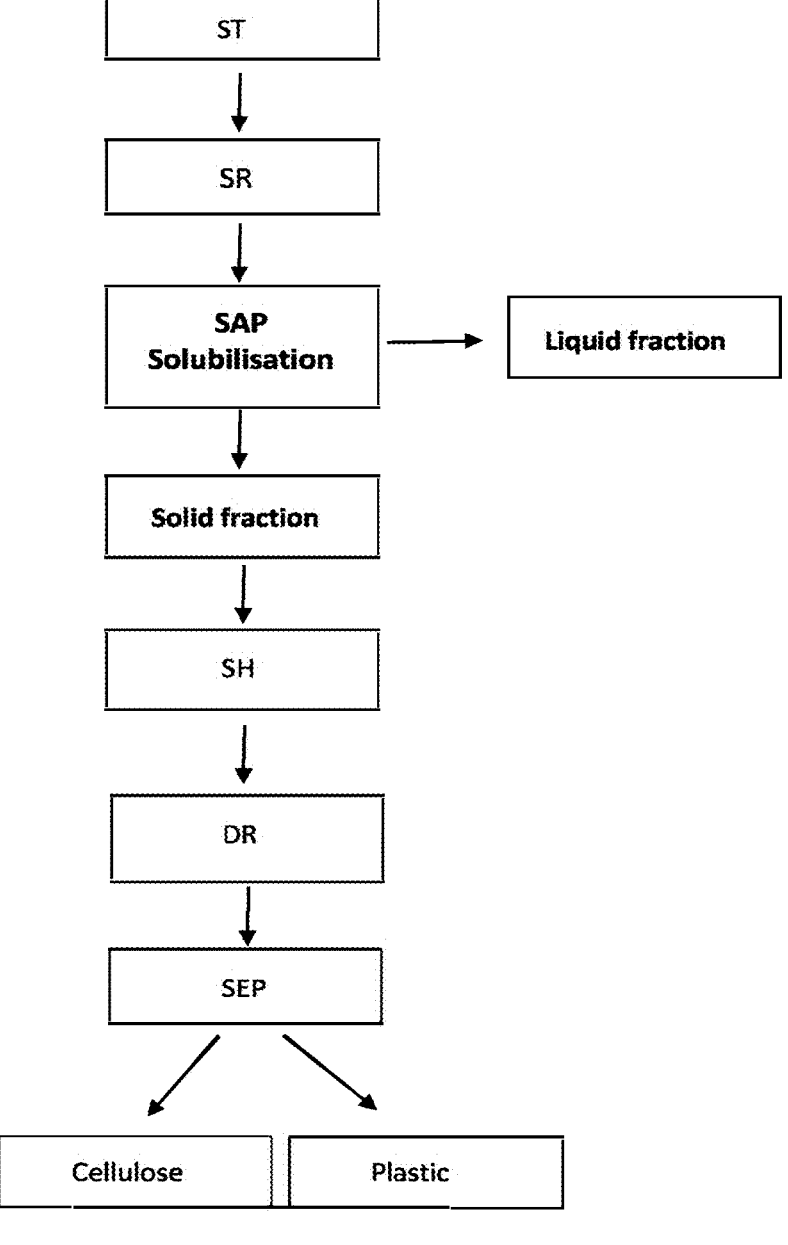
FIG. 3 represents a diagram of a method according to embodiments of the present description wherein the step for cross-link cleavage and solubilizing of the SAP is carried out by immersion of the sterilized post-consumer absorbent sanitary products.

As will be evident in the following description, the step for cross-link cleavage and solubilizing of the SAP can be carried out by direct immersion treatment of the sterilized post-consumer absorbent sanitary products (FIG. 3). Satisfactory results are also obtained when this step is carried out by immersion of the sterilized and also shredded products (FIG. 4), or when this step is carried out directly by immersion of the separated plastic and cellulose fractions (FIG. 5).

The treatment by immersion of the absorbent sanitary products to be treated may be carried out in a bath with an aqueous solution containing at least one oxidizing compound, preferably hydrogen peroxide, in an amount comprised between 5% and 50% (weight/weight) of this solution.

The step of treating by immersion can be advantageously carried out at a temperature between 65° C. and 100° C.

Furthermore, the products immersed in the bath can be subjected to a compression force exerted by a pressure ranging from 5 N/cm$^2$ to 20 N/cm$^2$, as described below.

The method has the advantage of not including steps configured for inactivating the SAP, for example, by treating the material with organic acids or inorganic acids.

The method allows products recovered from post-consumer material to be obtained-cellulose, plastic, linear polyacrylate (LPA)—wherein the quality is preserved for convenient re-use.

Figure 2:
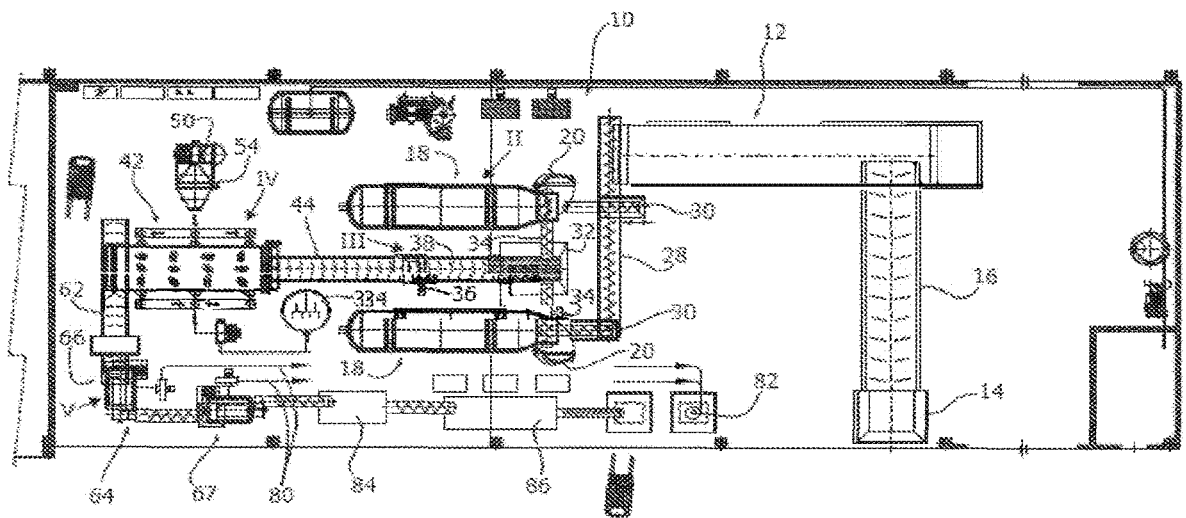
FIG. 2 is a plan view of an apparatus usable for the method schematized, for example, in FIG. 1.

In one or more embodiments, the method may comprise one or more of the steps schematically illustrated, for example, in FIG. 1, or rather, a sterilization step SR of post-consumer absorbent sanitary products, a shredding step SH of the sterilized products, a drying step DR of the sterilized and shredded products, a separation step SEP of the plastic and cellulose products, as described, for example, in the document WO 2018/060827 by the same Applicant and reported below. In particular, the method may comprise a collection step ST of the post-consumer absorbent sanitary products coming from the recycling collection in a storage container. FIG. 2 illustrates an apparatus 10 wherein the storage container is indicated by reference number 12. Waste collection vehicles unload post-consumer absorbent sanitary products into an unloading area 14 and a conveyor 16 loads the post-consumer absorbent sanitary products into the storage container 12. Collected post-consumer absorbent sanitary products may have a density in the order of 150-300 kg/m$^3$ and humidity in the order of 65-80%.

The total humidity of the material, understood as the percentage of water contained therein, is calculated from the dry weight of the sample (according to IRSA-CNR 1984—notebook 64 and UNI 936 UNICHIM 10506/1996 methods).

After the collecting step ST, the sterilization step SR follows, for example, carried out by loading the products in a rotary autoclave 18. In the example illustrated in FIG. 2, the apparatus 10 comprises two autoclaves 18, which are loaded alternately with post-consumer absorbent sanitary products coming from the storage container 12. A conveyor 28 picks up the products from the storage container 12 and transports them to the autoclave 18. Two loaders 30 load the products inside the respective autoclaves 18. During loading of the products, the door 20 of the autoclaves is opened, and the cylindrical body is rotated to progressively move the products towards the rear. Once loading has finished, the door 20 is closed and the autoclave 18 is heated and pressurized by direct and indirect supply of steam, until it reaches a temperature of about 135° C. and an internal pressure of about 3.1 bar.

In one or more embodiments, the sterilization step SR may be carried out by heating the post-consumer absorbent sanitary products at a temperature between 120° C. and 140° C. and at a pressure between 1 and 3.6 bar. During the sterilization treatment, the autoclave can be alternatively rotated in a clockwise and anticlockwise direction around its axis in order to allow the movement of the products contained therein.

The sterilization step SR has the object of heating the products to a temperature at which it is possible to obtain complete sterilization of the bacterial load. The sterilization step can be carried out for a time interval from 20 minutes to 2 hours. At the end of the sterilization treatment, the vapor contained within the autoclave 18 is extracted and purified in a scrubber 34. The door 20 is then opened and the body is rotated to discharge the products. In the example of FIG. 2, two autoclaves 18 are provided, which operate in an alternating manner. While a first autoclave 18 performs the sterilization treatment, the other autoclave 18 performs the operations of unloading sterilized material and loading of a new batch. In this way, it is possible to obtain an essentially continuous stream of sterilized material downstream of the autoclave 18.

At the end of the sterilization treatment, the sterilized material leaving the autoclave is collected in a storage vessel 32. The sterilized material leaving the autoclave may have a density of about 300-400 kg/m$^3$, a temperature of 80-100° C. and a total humidity in the order of 70-85%, calculated from the dry weight of the sample (according to IRSA-CNR 1984—notebook 64 and UNI 936 UNICHIM 10506/1996 methods).

From the storage vessel 32, the sterilized material is sent to a shredder 36 by means of a conveyor belt 38. The shredder may comprise, for example, two rotors driven by a motor. The rotors are provided with teeth that carry out shredding of the material. The shredding allows material to be obtained having a particle size of less than 10 cm, preferably less than 3 cm, more preferably less than 1 cm.

After shredding SH, the material may have a density of the order of 400-500 kg/m$^3$, a temperature of about 75-95° C. and a total humidity in the order of 70-85% calculated from the dry weight of the sample (according to IRSA-CNR 1984—notebook 64 and UNI 936 UNICHIM 10506/1996 methods).

The material subjected to the sterilization and shredding steps is sent by means of a conveyor 44 to a dryer 42 where the drying step DR is carried out. The dryer 42 comprises a casing within which horizontal perforated conveyors are housed, driven alternately in opposite directions and overlapping each other vertically. The conveyor 44 unloads the material onto the upper conveyor. At the outlet of each horizontal conveyor, the material falls onto the underlying conveyor. While the material is transported horizontally and passes sequentially from one conveyor to the underlying one, a flow of heated air passes through the casing from the bottom upwards. The flow of air passes through the perforated conveyors and the material located on them. The flow of air is generated by a fan 50 connected to a filter. The airflow is heated in a battery of heat exchangers 54 supplied with steam. The air flow leaving the heat exchanger 42 is aspirated by a second fan and is sent to a condensation discharge device 58 to a scrubber. At the outlet of the dryer 42, the material is unloaded onto a conveyor belt 62. The dryer 42 may be equipped with microwave generators facing the upper conveyor, to accelerate the heating of the material and increase the drying effect. The material at the inlet of the dryer has a temperature of about 70-90° C. The drying air temperature inside the dryer 42 is approximately 140° C.

The product leaving the dryer 42 has a temperature of about 50-70° C., a density of about 35-50 kg/m$^3$, and a total humidity in the order of 5-20%, calculated from the dry weight of the sample (according to IRSA-CNR 1984—notebook 64 and UNI 936 UNICHIM 10506/1996 methods).

Downstream of the drying step DR, the sterilized, shredded and dried material is sent to a separation assembly 64 in which the step of separating plastic and cellulose is performed.

The separation step may be carried out in at least one centrifugal separator. The separation assembly 64 may comprise, for example, at least one first centrifugal separator comprising a base and having an inlet for the material to be separated. In the example illustrated in FIG. 2, two centrifugal separators 66, 67 are provided in cascade.

The centrifugal separator 66 may comprise a separation chamber in which a perforated cylindrical filter is housed, within which a rotor is mounted, rotatable about a horizontal axis. The inlet material is projected radially outwards against the perforated filter. The cellulose has smaller dimensions than the plastic, and passes through the filter and is collected in a first outlet, while the plastic remains inside with respect to the filter and is collected in a second outlet. Preferably, the plastic leaving the first centrifugal separator 66 is sent to a second centrifugal separator 67 having a filter with smaller perforations. At the outlet of the centrifugal separators 66, the cellulose flows 80 may potentially be sent to a cellulose shredder and to a cellulose pelletizer 82. The plastic leaving the separator 66 may be sent to a plastic shredder 84 and, subsequently, to an extruder or densifier 86.

A method comprising the steps described above can make it possible to obtain cellulose with a purity of between 55% and 90%, and plastic with a purity of between 80% and 97%.

These values were determined by analysis in Fourier transform infrared spectrophotometry, FTIR (combined with ATR-Attenuated Total Reflectance for cellulose analysis, American Journal of Analytical Chemistry, 2018, Vol. 9, pages 303-310; FTIR combined with UNI EN ISO 6427/2013 and ISO 16152/2005 Methods for determining the purity of the plastic).

In particular, the separated cellulose may comprise an amount of residual SAP comprised between 5% and 15% by weight, on average in the order of 11%, according to an evaluation carried out with FTIR infrared spectrophotometry analysis.

The recovered plastic fraction may comprise, in addition to traces of cellulose, a residual SAP quantity of between 3% and 9% by weight, on average in the order of 5% by weight, according to an evaluation conducted with FTIR infrared spectrophotometry analysis.

The method subject of the present description, comprising a step for cross-link cleavage, solubilizing, removing and re-using the SAP, allows obtaining plastic and cellulose with a significantly higher degree of purity.

As schematized in FIG. 3, the step for cross-link cleavage and solubilizing of the SAP may be carried out, after the sterilizing step, by immersing the sterilized sanitary products in a bath with an aqueous solution comprising at least one oxidizing compound. This step may be carried out inside a thermally insulated (adiabatic) cylindrical reactor, bathed with the aqueous solution containing at least one oxidizing compound.

The aqueous solution may comprise at least one oxidizing compound, preferably hydrogen peroxide, in an amount comprised between 10% and 50% (weight/weight), preferably equal to 15% (weight/weight).

In one or more embodiments, the aqueous solution comprises at least one oxidizing compound, preferably hydrogen peroxide, in an amount comprised between 150% and 340% by weight with respect to the dry weight of said immersion-treated sterilized sanitary products.

Furthermore, the ratio between the volume of the aqueous solution containing at least one oxidizing compound and the weight of the sterilized post-consumer absorbent sanitary products to be treated with the aforesaid composition may be between 3 and 12 l/kg (liters/kg) (i.e. 3:1 and 12:1), preferably between 5 and 8 l/kg (i.e. 5:1 and 8:1). Advantageous results have been observed when the immersion step of the humid and hot material leaving the rotary autoclave 18 is carried out in a bath at room temperature. The immersed material may have a temperature between 80° C. and 100° C., a total humidity in the order of 70-85%, and a size between 3 cm and 80 cm.

Furthermore, optimal separation results of the SAP from the remaining solid components are obtained when the treated products are kept in constant movement by means of a mechanical stirring rod with fixed blades, at an adjustable speed from 0 to 120 revolutions per minute (rpm), preferably 60 rpm.

Furthermore, the Inventors have observed that even more advantageous results may be obtained if the sterilized post-consumer sanitary products placed in the bath are subjected to a compressive force exerted by, for example, a disc-headed piston with holes, preferably 1 cm in diameter, operated by a hydraulic pump, exerting pressure. The pressure exerted can be between 5 and 25 N/cm$^2$.

In general, the compression exerted on the material treated by immersion keeps all the mass of the material soaking, avoiding separation of the liquid fraction from the solid fraction. In fact, in the absence of adequate backpressure, the solid fraction would tend to separate from the aqueous solution containing the oxidizing reactive compound. The pressure exerted, preferably included in the aforesaid range, may be kept constant or variable; for example, it can increase at the end of the treatment step by immersion to facilitate the subsequent step of separating the liquid fraction from the solid fraction.

By adopting the operating conditions described, the immersion step in the bath may be carried out for a period of time less than 90 minutes, preferably between 55 minutes and 80 minutes.

The advantage of conducting the immersion and solubilization step of the SAP directly on the sterilized products and prior to the shredding step of the sterilized products consists in the fact that, as previously described, the products leaving the autoclave have a total humidity in the order of 70-85% and a temperature between 80° C. and 100° C. These characteristics allow:

1. reducing the volumes of water to be added for constituting the aqueous solution containing at least one oxidizing compound given the already high contribution of water present in the material;
2. minimizing the loss of the SAP in the form of granules in the subsequent shredding, drying and mechanical separation steps, since the SAP has been extracted as soluble LPA;
3. minimizing cellulose and plastic contamination since the SAP was extracted as soluble LPAs;

4. reducing, as a consequence of point 1, the heat maintenance times of the subsequent drying step DR;

5. obtaining, as a consequence of point 3, high purity cellulose and plastic fractions;

6. not heating the reactor for the entire action time of the solution with the oxidizing compound as the material itself exchanges heat with the solution activating it accordingly.

The immersion treatment makes it possible to obtain a suspension that comprises i) a mixed solid fraction comprising cellulose and plastic and ii) a liquid fraction containing the solubilized SAP, in particular non-cross-linked linear polyacrylate (LPA).

The solid fraction may be separated from the liquid fraction, for example, by further compression of the material. By exerting pressure by means of a hydraulic piston, the solution is allowed to rise above the perforated head of the piston. The pressure may be between 10 and 25 N/cm$^2$. An outflow valve allows the collection of the waste solution (liquid fraction). The liquid fraction may be subjected to a purification step, for example, by filtration on disc filters.

The solid fraction comprising the plastic and cellulose fractions purified from the SAP may then be subjected to shredding SH, drying DR, and separation SEP, as described. Before transporting the material to the shredder, the solid fraction comprising cellulose and plastic may possibly be subjected to at least one washing step, preferably with water, in the same adiabatic reactor, in order to recover further SAP residues. Solutions collected by means of the outflow valve can be pooled.

Downstream of the shredding step SH, conducted as described in the previous sections, the solid fraction may be dried, preferably inside a dryer wherein the drying air temperature is between 100° C. and 140° C. Downstream of the drying step, the separation step SEP of the cellulose from the plastic can follow, preferably with at least one centrifugal separator, as described in the previous sections.

Cellulose and plastic thus obtained have a purity greater than 99%. Purity and identity of the solid fractions obtained by the method described were determined and confirmed by analysis in Fourier transform infrared spectrophotometry, FTIR, combined with ATR-Attenuated Total Reflectance for analysis of the cellulose, American Journal of Analytical Chemistry, 2018, Vol. 9, pages 303-310; and FTIR combined with the UNI EN ISO 6427/2013 and ISO 16152/2005 Methods for analysis of the plastic).

Figure 4:
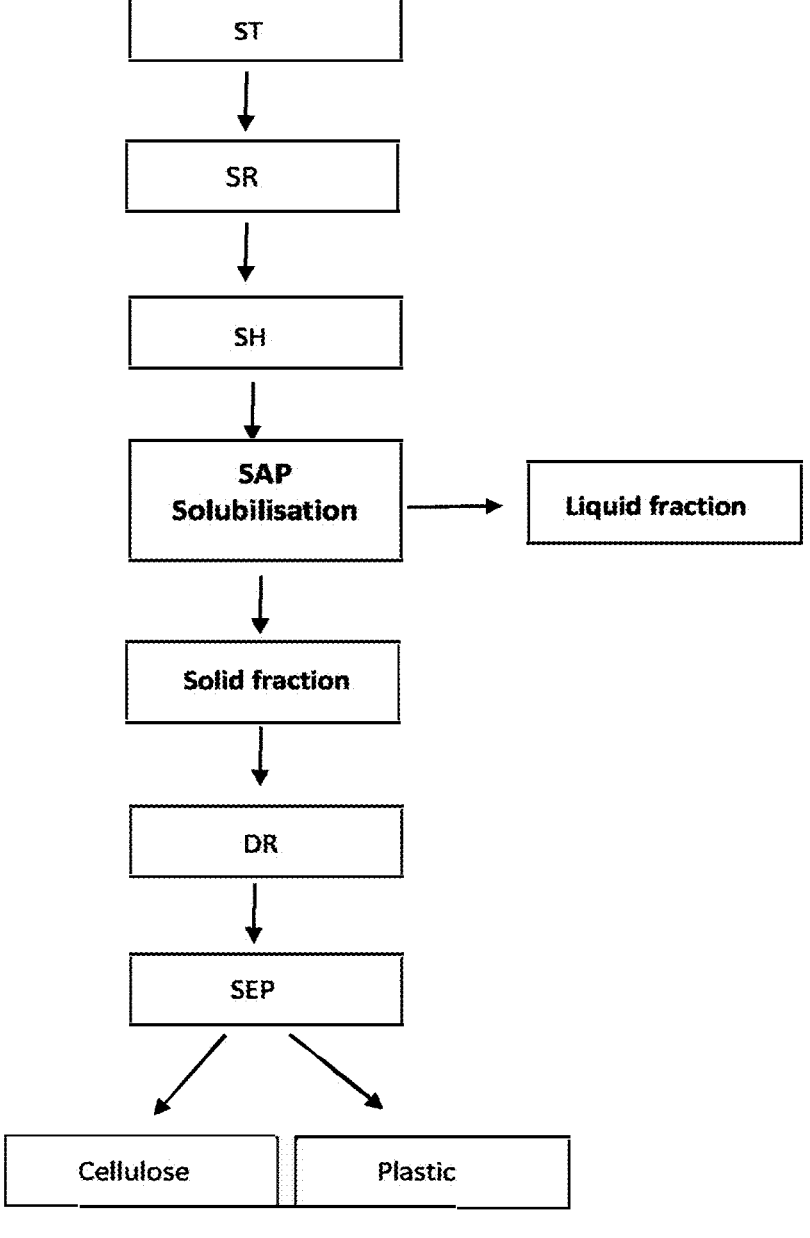
FIG. 4 represents a diagram of a method according to embodiments of the present description wherein the step for cross-link cleavage and solubilizing of the SAP is carried out by immersion of the shredded and sterilized post-consumer absorbent sanitary products.
Figure 5:
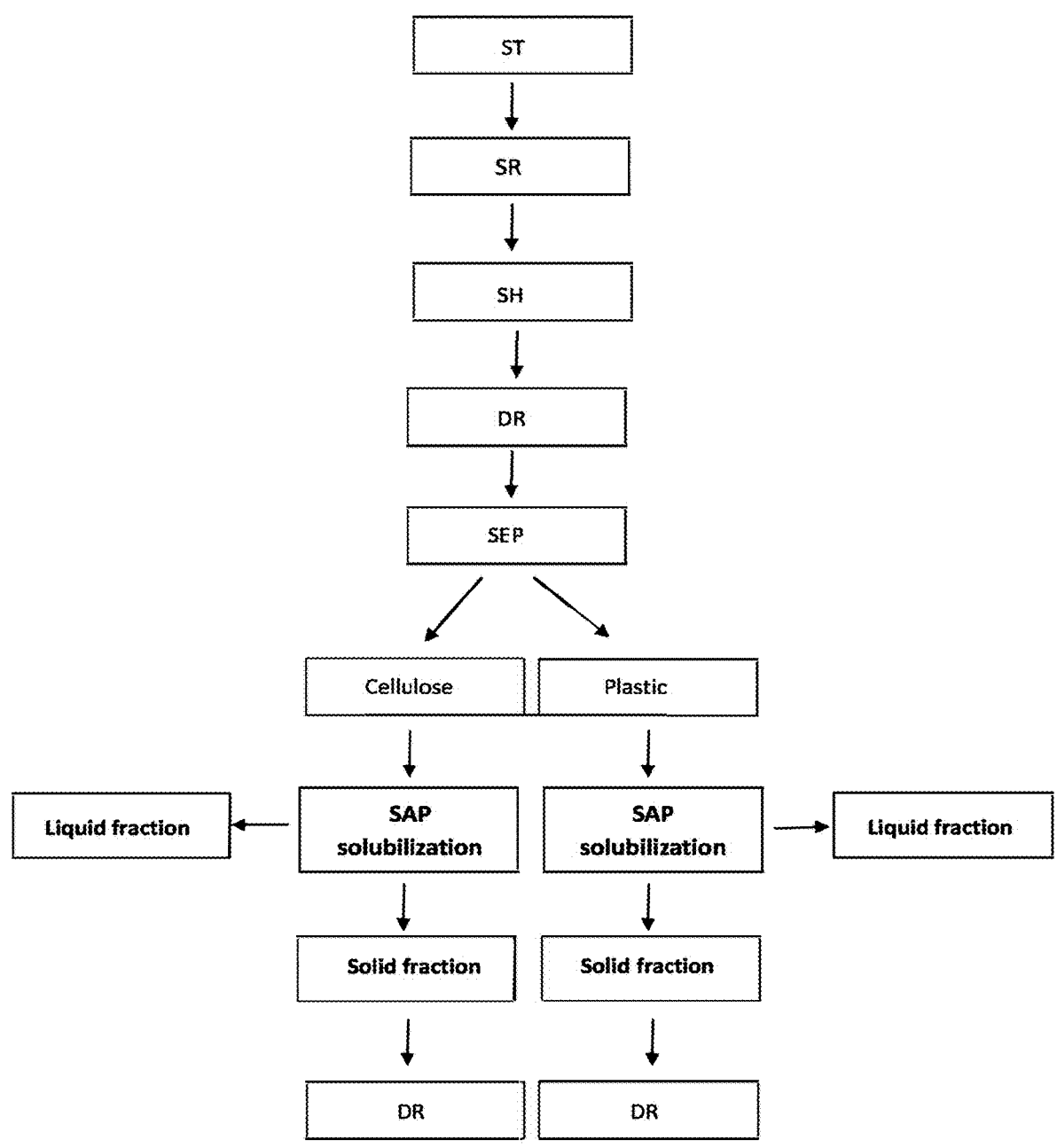
FIG. 5 represents a diagram of a method according to embodiments of the present description wherein the step for cross-link cleavage and solubilizing of the SAP is carried out by immersion of the separated cellulose and plastic fractions.

FIG. 4 illustrates a method that comprises the steps of sterilization SR, shredding SH, drying, DR and separation SEP, as described in the preceding sections. FIG. 4 also illustrates that the step of solubilizing the SAP is carried out downstream of the shredding step SH, i.e. on sterilized and shredded post-consumer absorbent sanitary products. In particular, the treated material has a particle size between 1 cm and 10 cm, a temperature between about 75° C. and 95° C. and a total humidity from 70% to 85%.

The sterilized and shredded products are immersed in a bath with an aqueous solution comprising an oxidizing compound, preferably inside an adiabatic cylindrical reactor.

The aqueous solution comprises at least one oxidizing compound, preferably hydrogen peroxide, in an amount comprised between 10% and 50% (weight/weight), preferably equal to 15% (weight/weight).

In one or more embodiments, the aqueous solution comprises at least one oxidizing compound, preferably hydrogen peroxide, in an amount comprised between 150% and 340% by weight with respect to the dry weight of said immersion-treated sterilized and shredded sanitary products.

Furthermore, the ratio between the volume of the aqueous solution containing at least one oxidizing compound and the weight of the sterilized and shredded post-consumer absorbent sanitary products to be treated with the aforesaid composition may be between 3 and 12 l/kg (i.e. between 3:1 and 12:1), preferably between 5 and 8 l/kg (i.e. between 5:1 and 8:1).

Advantageous results have been observed when the immersion step of the humid and hot material transported by the conveyor 44 is carried out in a bath at room temperature. The immersed material may have a temperature between 75° C. and 95° C., and a total humidity in the order of 70-85%.

Optimal separation results of the SAP from the remaining solid components are obtained, in this case as well, when the material is kept in constant movement by means of mechanical stirring rod with fixed blades, at an adjustable speed from 0 to 60 revolutions per minute (rpm), preferably 30 rpm.

Furthermore, the Inventors have observed that even more advantageous results may be obtained if the sterilized post-consumer sanitary products placed in the bath are subjected to a compressive force exerted by, for example, a disc-headed piston with holes of 1 cm in diameter, operated by a hydraulic pump, exerting pressure. The pressure exerted can be between 5 and 20 N/cm$^2$.

In general, the compression exerted on the material treated by immersion keeps all the mass of the material soaking, avoiding separation of the liquid fraction from the solid fraction. In fact, in the absence of adequate backpressure, the solid fraction would tend to separate from the aqueous solution containing the oxidizing compound.

By adopting the operating conditions described, the immersion step in the bath may be carried out for a period of time between 30 minutes and 45 minutes, not greater than 60 minutes.

Furthermore, similarly to what has been observed with reference to FIG. 3, advantageous results have been observed when the immersion and solubilization step of the SAP proceeds directly on the sterilized and shredded products placed in immersion and subjected to a compression force.

The advantages derive from the fact that, as previously described, the shredded products transported by the conveyor 44 have a temperature of about 75-95° C. and a total humidity in the order of 70-85%, calculated from the dry weight of the sample (according to IRSA-CNR 1984—notebook 64 and UNI 936 UNICHIM 10506/1996 methods). These characteristics allow:

1. reducing the volume of water to be added for constituting the aqueous solution containing at least one oxidizing compound given the already high contribution of water present in the material;

2. minimizing the loss of SAP in the form of granules in the subsequent drying and mechanical separation steps, since the SAP has been extracted as soluble LPA;

3. minimizing cellulose and plastic contamination since the SAP was extracted as soluble LPA;

4. reducing, as a consequence of point 1, the heat maintenance times of the subsequent drying step DR;

5. obtaining, as a consequence of point 3, high purity cellulose and plastic fractions;

6. not heating the reactor for the entire action time of the aqueous solution, as the material itself exchanges heat with the solution, activating it accordingly.

The treatment to solubilize the SAP carried out as described involves forming a suspension comprising i) a mixed solid fraction containing plastic and cellulose purified from the SAP and ii) a liquid fraction comprising the solubilized SAP.

The mixed solid fraction may be separated from the liquid fraction, by further compression of the material. By exerting pressure, for example, by means of a hydraulic piston, the solution is allowed to rise above the perforated head of the piston. The pressure may be between 10 and 25 N/cm². An outflow valve allows collection of the waste solution (liquid fraction).

The liquid fraction may be subjected to a purification step, for example, by means of filtration on disc filters.

The solid fraction, separated from the liquid phase, may be subjected to the subsequent drying DR and separation SEP steps, preferably carried out with at least one centrifugal separator, as described in the previous sections. Before transporting the material to the dryer, the mixed solid fraction comprising cellulose and plastic may possibly be subjected to at least one washing step, preferably with water, in the same adiabatic reactor, in order to recover further SAP residues. Fractions collected by means of the outflow valve can be pooled.

Downstream of the drying step carried out as described in the preceding sections, the step of separating the cellulose from the plastic may follow, preferably with at least one centrifugal separator, as described in the previous sections.

Cellulose and plastic thus obtained have a purity greater than 99%. Purity and identity of the solid fractions obtained by the method described were determined and confirmed by analysis in Fourier transform infrared spectrophotometry, FTIR, combined with ATR-Attenuated Total Reflectance for analysis of the cellulose, American Journal of Analytical Chemistry, 2018, Vol. 9, pages 303-310; and FTIR combined with the UNI EN ISO 6427/2013 and ISO 16152/2005 Methods for analysis of the plastic).

As illustrated in FIG. 5, the step for cross-link cleavage and solubilizing of the SAP may be carried out downstream of the separation step SEP of the cellulose fraction from the plastic fraction.

In this case, the method comprises the steps of sterilizing SR the post-consumer absorbent sanitary products, drying DR the sterilized material, possibly shredding SH the sterilized material, separating SEP the cellulose fraction from the plastic fraction from the sterilized and dried material, treating the cellulose fraction and/or the plastic fraction by immersion in a bath with an aqueous solution containing at least one oxidizing compound preferably selected from the group consisting of sodium persulfate, potassium persulfate, ammonium persulfate, potassium monopersulfate, and hydrogen peroxide, to cleave the cross-links and solubilize the SAP contained in said cellulose fraction and said plastic fraction and obtaining a suspension comprising i) a solid phase containing the cellulose fraction and/or the plastic fraction and ii) a liquid fraction containing linear polyacrylate (LPA).

In particular, the cellulose fraction and/or the plastic fraction separated at room temperature are immersed, each inside a respective and preferably distinct reactor, preferably an adiabatic and heatable cylindrical reactor, in a bath with the aqueous solution containing at least one oxidizing compound.

The ratio between the volume of the aqueous solution containing at least one oxidizing compound, preferably hydrogen peroxide, and the weight of each cellulose and plastic fraction to be treated with the aforesaid composition is between 10 and 30 l/kg (i.e. between 10:1 and 30:1), preferably between 17 and 25 l/kg (i.e. between 17:1 and 25:1).

In the case of treatment by immersion of the cellulose fraction, the aforesaid ratio is preferably between 10 and 30 l/kg, preferably between 14 and 25 l/kg. In the case of treatment by immersion of the plastic fraction, the ratio is preferably between 10 and 25 l/kg, more preferably between 12 and 22 l/kg.

In one or more embodiments, the aqueous solution comprises hydrogen peroxide in an amount ranging from 150% to 300% by weight with respect to the dry weight of said cellulose fraction or said immersion-treated plastic fraction.

In one or more embodiment, treating said cellulose fraction by immersion may be carried out in an aqueous solution containing at least one oxidizing compound, preferably hydrogen peroxide, in an amount comprised between 10% and 50% (weight/weight), more preferably equal to 15% (weight/weight).

Optimal results were observed when the immersion treatment of the plastic fraction was carried out in an aqueous solution containing hydrogen peroxide in an amount ranging from 5% to 50% (weight/weight), preferably equal to 10% (weight/weight).

In one or more embodiments, the immersion treatment step is carried out at a temperature from 65° C. to 100° C. Preferably, the step of treatment by immersion of the cellulose fraction is carried out at a temperature of 85° C.; the step of immersion of the plastic fraction can preferably be carried out at a temperature of 75° C. The bath can be heated by means of heat exchange to be carried out or by circulating a heat transfer fluid in a coil, or by ohmic heating carried out by means of electric resistances.

In one or more embodiments, the step of treating the cellulose fraction by immersion can be carried out for a period of time ranging from 20 minutes to 60 minutes, preferably for a period of 35 minutes.

In one or more embodiments, the step of treating the plastic fraction by immersion can be carried out for a period of time ranging from 15 minutes to 40 minutes, preferably for a period of 20 minutes.

The efficiency of the SAP dissolution process depends on the time of action of the oxidizing composition, which, after the initial thermal activation, proceeds rapidly until its maximum action is exhausted within the indicated times, after which a plateau condition is reached, independent of the time.

The inventors have also observed that optimal results are obtained when, during the step of treating by immersion, the cellulose fraction and/or the plastic fraction are subjected to a compression force.

The compression may be carried out, for example, by means of a piston with a perforated disc head, preferably with holes of 1 cm in diameter, operated by a hydraulic pump, exerting a pressure between 5 and 20 N/cm² for the cellulose, and between 5 and 20 N/cm², preferably from 5 to 15 N/cm² for the plastic fraction.

In general, the compression exerted on the material treated by immersion (FIGS. 3 to 5) allows a series of advantages to be obtained. The compression avoids the separation of the liquid fraction from the solid fraction. In fact, in the absence of adequate backpressure, the solid fraction would tend to separate from the aqueous solution containing the oxidizing compound. Due to the convective currents generated when hot, the development of oxygen and water vapor, and the different density of the solid components, the latter would be pushed upwards and stationed above the liquid mass.

The compression exerted on the solid fractions (cellulose and plastic together (mixed solid fraction) or cellulose and plastic separately) also allows:

maintaining the optimal ratio between the volume of the aqueous solution containing at least one oxidizing compound and the weight of the solid fraction, since the material to be treated is not very dense and compressible. This allows containing the volume of the aqueous solution to be used to keep the materials to be treated soaking;

keeping the material to be treated (cellulose and plastic together or cellulose and plastic separately) soaking in the aqueous solution containing at least one oxidizing compound, for the entire duration of the immersion step. Furthermore, at the end of the immersion period, it is also possible to further increase the pressure so as to compress the solid fraction on the bottom of the reactor and allow an optimal separation of the liquid fraction, which is pushed upwards through the holes contained in the head of the piston;

facilitating any washing cycles of the cellulose fraction and the plastic fraction once separated from the liquid fraction containing linear polyacrylate (LPA);

containing the volumes of waste water, downstream of the aforesaid cycles, even not more than double the initial volume of the oxidizing solution to be used.

The treatment step by immersion can be carried out by stirring using a mechanical stirring rod with a fixed blade, at an adjustable speed from 0 to 60 revolutions per minute (rpm), preferably 30 rpm.

The method described here may further comprise a step of separating the solid phase from the liquid phase. The separation step can be carried out by opening a lateral outflow valve or by suction.

In one or more embodiments, the method may also comprise at least one washing step of the solid phase, preferably carried out with water, in order to recover additional residues derived from SAP. The solid phase (cellulose/plastic) may be subjected to drying, for example, in a dryer as described in the previous sections.

The liquid phase separated from the solid fraction downstream of the immersion treatment step of the plastic fraction may contain an overall solid residue between 1.0 and 15.5 g/L, on average between 2.7 and 3.6 g/L.

The liquid phase separated from the solid fraction downstream of the immersion treatment step of the cellulose fraction may contain an overall solid residue between 6.1 g/L and 11.3 g/L.

The liquid phase separated from the solid fraction downstream of the immersion treatment step of the mixed fraction leaving the shredder may contain an overall solid residue between 7 g/L and 13 g/L.

The liquid phase separated from the solid fraction downstream of the immersion treatment step of the mixed fraction leaving the autoclave may contain an overall solid residue between 8 g/L and 12 g/L.

The liquid phases recovered following the solubilization of the SAP conducted downstream of the sterilization, or sterilization and shredding, or sterilization, shredding and drying, or sterilization, shredding, drying and separation steps can be used to conduct cross-linking methods of linear polyacrylate (LPA) to obtain super-absorbent polymers based on polysaccharides (polysaccharide-based SAP) as described, for example, in the document US 2017/0022671 according to two modalities: i) addition of cross-linking agent and activator and ii) addition of monomer, cross-linking agent and activator (document U.S. Pat. No. 4,295,987. Cross-linked absorbent sodium polyacrylate; document U.S. Pat. RE.32,649E, Hydrogel-forming polymer compositions for use in absorbent structures).

According to modality i), the cross-linker N,N'-methylene bis(acrylamide), MBA, is added to the reactor containing the liquid phase-after removing the dissolved oxygen by bubbling nitrogen—in an amount between 0.01 and 0.5% (weight/volume), preferably equal to 0.15 (weight/volume; g/ml). Consequently, the activator, or rather, an ammonium or potassium persulfate (APS or KPS), is added in an amount between 0.1 and 0.8% (weight/volume). Precipitation of the cross-linked polymer is observed within 1 hour by carrying out the reaction at 75° C.

According to the procedure described in point ii), the monomer (acrylamide (AM) or acrylic acid (AA) or methacrylic acid (MA) or a sodium or potassium salt thereof) is added to the reactor containing the liquid fraction-after having removed the dissolved oxygen by bubbling nitrogen) in a quantity ranging from 1% to 7% (weight/volume), preferably equal to 4.7%. Furthermore, the activator, or rather, an ammonium or potassium persulfate (APS or KPS), is added in an amount from 0.1 to 0.8% (weight/volume). After 1 hour, the pH is brought to alkaline values with NaOH at 10%, then the cross-linking agent (MBA) is added in an amount from 0.01% to 0.5%, preferably 0.15% (weight/volume; g/ml). Precipitation of the cross-linked polymer is observed after at least 1 hour by carrying out the reaction at 80° C.

The method may also comprise at least one purification step of the liquid fraction, preferably carried out by filtration carried out with disc filters.

The purified liquid fraction containing linear polyacrylate (LPA) can be used for cross-linking methods of the LPA and production of new SAP.

For example, the purified liquid fraction can be subjected to a subsequent cross-linking step by exchange of calcium ions or other divalent or trivalent metals (Me) using the monovalent alkaline metal typical of LPA, preferably sodium or potassium. The cross-linking step, carried out as described, for example, in U.S. Pat. No. 5,558,745, allows an insoluble compound (polyacrylate-metal (PA-Me)) to be obtained, which can be separated by filtration. Calcium salts (or salts of other divalent or trivalent metals) allow cross-linking since the polydentate metal binds two or more carboxylate groups to itself, binding the linear chains with bridges. The salts that can be used include chlorides, sulphates, nitrates, calcium carbonates, magnesium, zinc and aluminum, preferably calcium chloride, even more preferably calcium nitrate, the latter being more soluble and inert. Calcium salts may be used in quantities (weight/volume) ranging from 1% to 5% (weight/volume), preferably equal to 3% (weight/volume). Once the precipitation of the polyacrylate bound to the metal is obtained, the solvent can be evaporated to obtain a transparent solid material.

The purified liquid fraction, preferably by filtration, may also be subjected to a cross-linking step of the acrylate polymers in linear form by adding a cross-linking agent and a radical activator, as described, for example, in U.S. Pat. No. 4,295,987. Briefly, the cross-linker N,N'-methylene-bis (acrylamide) (MBA) is added to the purified liquid phase contained in a reactor or tank-after removing the dissolved oxygen by bubbling nitrogen, and keeping the atmosphere inert—the amount of MBA ranging from 0.02 to 0.25% (g/l), preferably equal to 0.12% (g/ml). Consequently, an activating compound is added at room temperature, such as, for example, ammonium or potassium persulfate (APS or KPS) in an amount between 0.1% and 0.8% (weight/volume). The reaction carried out at 60° C. for a period of 2 hours involves the precipitation of the cross-linked polymer.

The purified liquid fraction, preferably by filtration, may also be subjected to cross-linking by adding monomers in addition to the cross-linking agent and activator. The monomer (acrylamide, AM, or acrylic acid (AA) or methacrylic acid (MA) or a sodium or potassium salt thereof is added in quantities ranging from 0.5% (weight/volume) to 7% (weight/volume) volume), preferably 4% (weight/volume). An activating compound is subsequently added, or rather, ammonium or potassium persulfate (APS or KPS), in an amount between 0.1 and 0.8% (weight/volume). After a period of 1 hour, the pH is brought to alkaline values with the addition of 10% NaOH, and the temperature in the reactor is brought to 60° C. for at least 3 hours. Finally, the cross-linking agent (MBA) is added in amounts ranging from 0.04% to 0.15% in moles with respect to the monomer (preferably 0.08% mol/mol) and the activator compound is added, under the same conditions described above.

As demonstrated in the example below, the described method allows whitening the cellulose without damaging the polysaccharide skeleton and—at the same time-allows cross-link cleavage and solubilizing of the SAP to obtain linear polyacrylate (LPA).

The cellulose obtained with the described method has a SAP content lower than 1% (weight/weight) and has a purity higher than 99%. Purity and integrity of the cellulose obtained from the described method were determined and confirmed by analysis in Fourier transform infrared spectrophotometry, FTIR, combined with ATR-Attenuated Total Reflectance, American Journal of Analytical Chemistry, 2018, Vol. 9, pages 303-310.

Furthermore, the method allows preserving the polyolefins that make up the plastic fraction and—at the same time-obtaining the cross-link cleavage and solubilization of the SAP.

The plastic obtained with the described method has a SAP content lower than 1% (weight/weight) and has a purity higher than 95%. The purity and integrity of the fraction containing plastics obtained from the described method were determined and confirmed by analysis in Fourier transform infrared spectrophotometry, FTIR, combined with the UNI EN ISO 6427/2013 and ISO 16152/2005 Methods.

EXAMPLES

1. Conduction of the Step to Solubilize SAP on the Mixed Cellulose and Plastic Fraction (FIG. 3).

Post-consumer absorbent sanitary material was sterilized in an autoclave at 135° C. for 20 minutes at a pressure of 2.1 bar.

At the end of the sterilization treatment, the sterilized material leaving the autoclave is collected in a storage vessel 32, as described in the preceding sections. Said collector may also have reactor functions.

Cellulose+Plastic (Particles Between 10 cm and 35 cm in Size Comprising SAP)

The mixed fraction composed of cellulose, plastic and SAP, with a total humidity of 82% and a temperature of about 96° C., is treated in a 1500 liter cylindrical stainless steel adiabatic reactor. The reactor has a rod with fixed blades for mechanical stirring; 81 liters of a 30% commercial hydrogen peroxide solution in water v/V, density 1.11 kg/L (300% with respect to the dry amount) are fed into the cold reactor with another 60 L of water (final oxidant concentration about 15% by weight with respect to the total water). A total of 50 kg of mixed material, wet at 82% by weight and with a temperature of about 96° C., are transferred into the reactor, and a disc-headed piston with holes of 1 cm in diameter, operated by a hydraulic pump, closes the head of the cylindrical reactor, exerting pressure of 8 N/cm$^2$ on the material. The piston stroke is stopped when the liquid level emerges beyond the surface of the disc by means of a level sensor. The stirring of the blade rod is activated for 80 minutes. After this period, the material is completely compressed by exerting a pressure of 25 N/cm$^2$ on the material, and the solution is allowed to rise above the perforated head of the piston. An outflow valve allows the collection of the waste solution. Two subsequent cycles with 50 L, which can be carried out with water only, allow the recovery of any traces of residual LPA from the first stage of the process. The solid mass remains in the reactor with residual moisture of 36% by weight. A 1 L fraction of the aqueous extract recovered downstream of a washing step was dried in an oven at 120° C. A stratified material suitable for the analysis of films by infrared spectrophotometry (FTIR combined with ATR) is recovered. The sample is placed in direct contact with the transmission crystal for ATR, revealing the presence of an IR spectrum compatible with the LPA. Dissolved in deuterated water, the dry compound was also analyzed by carbon nuclear magnetic resonance spectrometry $^{13}$C-NMR, revealing the absence of the signal at about 84 ppm, characteristic of the intramolecular cross-links of the SAP (Liu, Z. S., Rempel, G. L., Preparation of SAP by cross-linking Acrylic Acid and Acrylamide Copolymers, Appl Polym Sci 64:1345-1353, 1997).

The wet solid fraction is recovered from the bottom of the reactor. To check for any SAP residues, an aliquot of about 100 g was dried at 120° C. up to constant weight (in order to be able to express the degree of purity), reduced to particles smaller than at least 3 cm, and subjected to separation by means of a density fractionation carried out in water (as, for example, described in US 2015/0238974 A1-Liquid Density Separation System). The less dense plastic fraction will float in the device, while the cellulosic fraction will sink to the bottom. The two fractions are thus taken separately for evaluating the degree of residual SAP contamination. The analysis is conducted by FTIR infrared spectrophotometry combined with ATR. Both components do not have over 1% SAP contamination.

Therefore almost all of the SAP derivative passes into the recovery water after at least two washing cycles.

Chemical analyzes confirm that the two cellulose-based and plastic-based fractions are also compliant with the provisions of DECREE May 15 2019, no. 62—Regulation governing the termination of the qualification of waste from absorbent products for the person, pursuant to Article 184, paragraph 2, of Legislative Decree 3 Apr. 2006, no. 152.

2. Conduction of the Step to Solubilize SAP on the Mixed Cellulose and Plastic Fraction (FIG. 4).

Post-consumer absorbent sanitary material was sterilized in an autoclave at 135° C. for 20 minutes at a pressure of 2.1 bar.

The sterilized material was shredded in a shredder to obtain material with a size of less than 10 cm.

At the end of the shredding treatment, the sterilized and shredded material is transferred from the conveyor 44 into a reactor that precedes the dryer.

Cellulose+Plastic (Particles Between 3 cm and 10 cm in Size Comprising SAP)

The mixed fraction composed of cellulose, plastic and SAP, with a total humidity of 77% and a temperature of about 75° C., is treated in a 1500 liter cylindrical stainless steel adiabatic reactor. The reactor has a rod with fixed blades for mechanical stirring; 104 liters of a 30% commercial hydrogen peroxide solution in water v/V, density 1.11 kg/L (301% with respect to the dry amount) are fed into the reactor with another 90 L of water (final oxidant concentration about 15% by weight with respect to the total water). A total of 50 kg of mixed material, wet at 77% by weight and with a temperature of about 75° C., are transferred into the reactor, and a disc-headed piston with holes of 1 cm in diameter, operated by a hydraulic pump, closes the head of the cylindrical reactor, exerting pressure of 6 N/cm² on the material. The piston stroke is stopped when the liquid level emerges beyond the surface of the disc by means of a level sensor. The stirring of the blade rod is activated and an additional overheating is carried out up to 75° C., maintained for 40 minutes. After this period, the material is completely compressed by exerting a pressure of 22 N/cm² on the material, and the solution is allowed to rise above the perforated head of the piston. An outflow valve allows the collection of the waste solution. Two subsequent cycles, each with 50 L, which can be carried out with water only and in the cold, allow the recovery of any traces of residual LPA from the first stage of the process. The solid mass remains in the reactor with residual moisture of 33% by weight. A 1 L fraction of the aqueous extract recovered downstream of a washing step was dried in an oven at 120° C. A stratified material suitable for the analysis of films by infrared spectrophotometry (FTIR combined with ATR) is recovered. The sample is placed in direct contact with the transmission crystal for ATR, revealing the presence of an IR spectrum compatible with the LPA. Dissolved in deuterated water, the dry compound was also analyzed by carbon nuclear magnetic resonance spectrometry $^{13}$C-NMR, revealing the absence of the signal at about 84 ppm, characteristic of the intramolecular cross-links of the SAP (Liu, Z. S., Rempel, G. L., Preparation of SAP by cross-linking Acrylic Acid and Acrylamide Copolymers, Appl Polym Sci 64:1345-1353, 1997).

The wet solid fraction is recovered from the bottom of the reactor. To check for any SAP residues, an aliquot of about 100 g was dried at 120° C. up to constant weight (in order to be able to express the degree of purity), and subjected to separation by means of a density fractionation carried out in water (as, for example, described in US 2015/0238974 A1-Liquid Density Separation System). The less dense plastic fraction will float in the device, while the cellulosic fraction will sink to the bottom. The two fractions are thus taken separately for evaluating the degree of residual SAP contamination. The analysis is conducted by FTIR infrared spectrophotometry combined with ATR. The solid samples are placed in direct contact with the transmission crystal for ATR, allowing the recording of the typical IR spectra of the cellulose and plastic fractions. Both components do not have more than 1% SAP contamination.

Therefore almost all of the SAP derivative passes into the recovery water after at least two washing cycles.

Chemical analyzes confirm that the two cellulose-based and plastic-based fractions are also compliant with the provisions of DECREE May 15, 2019, no. 62—Regulation governing the termination of the qualification of waste from absorbent products for the person, pursuant to Article 184, paragraph 2, of Legislative Decree 3 Apr. 2006, no. 152.

3. Conduction of the Step to Solubilize SAP on the Cellulose Fraction and on the Plastic Fraction (FIG. 5).

Post-consumer absorbent sanitary material was sterilized in an autoclave at 135° C. for 20 minutes at a pressure of 2.1 bar.

The sterilized material was shredded in a shredder to obtain material with a size of less than 3 cm.

The material subjected to sterilization and shredding was subjected to drying carried out in a dryer in which the drying air had a temperature of about 140° C.

Downstream of the drying step, the material was separated into a cellulose fraction and a plastic fraction by using a centrifugal separator exploiting the different density of the two fractions, as described in the previous sections.

Cellulose (Particles Smaller than 3 cm Comprising SAP)

Figure 6:
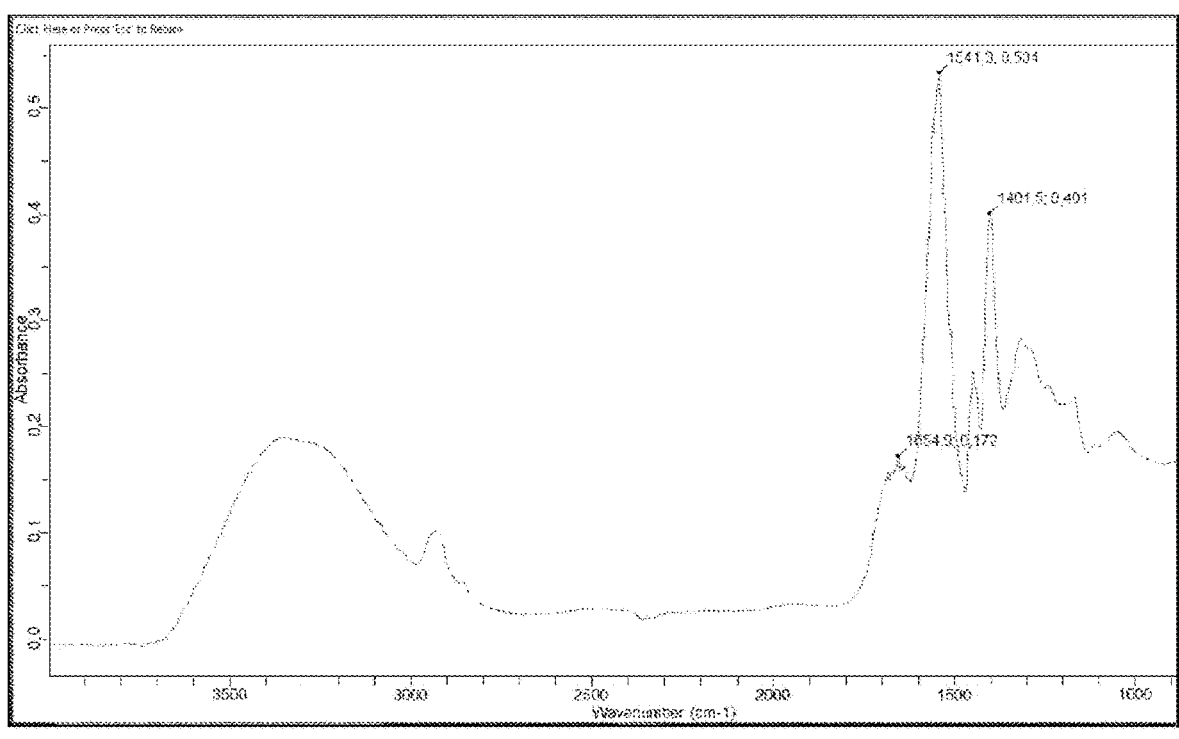
FIG. 6 shows a comparison between the IR spectra of LPA obtained in the liquid fraction derived from the method described (above) and LPA from a database (below, Spectra DataBase: Spectrum ID 8XQMEFCFImm, Copyright© 1980, 1981-2018 Bio-Rad Laboratories, Inc.)
Figure 6:
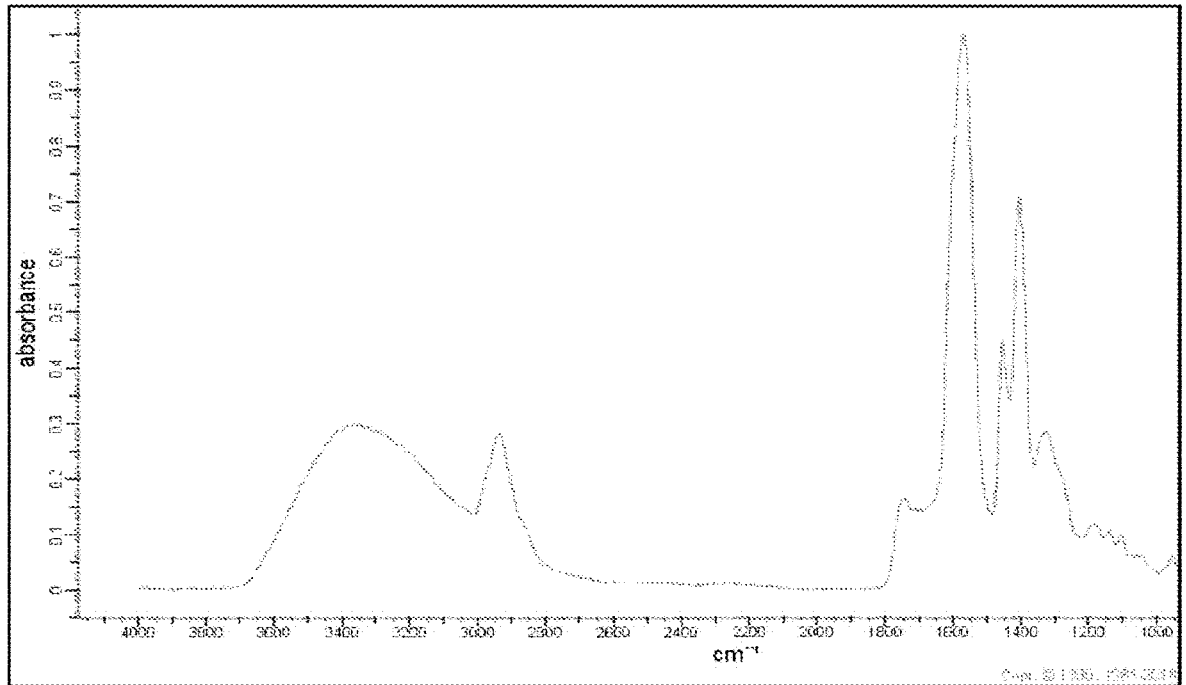

The cellulose fraction was treated in a 1500 liter cylindrical stainless steel adiabatic reactor, which was thermostatable through heat exchange to be carried out or through the circulation of a heat transfer fluid in a coil, or through ohmic heating achieved through electrical resistances. The reactor used has a rod with fixed blades for mechanical stirring. A total of 419 liters of a commercial 30% hydrogen peroxide solution in water v/V, density 1.11 kg/L (300% with respect to the dry amount) were fed into the reactor with another 550 L of water (final oxidant concentration about 15% in weight compared to water), and heated to a temperature of 70° C. A total of 50 kg of wet cellulose at 7% and with a temperature of about 20° C. were transferred to the reactor and placed in a bath to obtain a suspension. A disc-headed piston with 1 cm diameter holes, operated by a hydraulic pump, closes the head of the cylindrical reactor, exerting a pressure of 6 N/cm² on the material. The piston stroke is stopped when the liquid level emerges beyond the surface of the disc by means of a level sensor. The stirring of the blade rod is activated and additional overheating is obtained until reaching a temperature of 85° C. in the bath, a temperature that was maintained for 35 minutes. After this period of time, the material is completely compressed by exerting a pressure of 20 N/cm² on the material, to allow the solution to rise above the perforated head of the piston. An outflow valve allows the collection of the waste solution (liquid fraction). Two washing cycles of 75 L each, carried out with only water and in the cold, allow the recovery of any traces of residual LPA from the first stage of the process. A 1 L fraction of the liquid fraction recovered downstream of a washing step was dried in an oven at 120° C. A stratified material suitable for the analysis of films by infrared spectrophotometry (FTIR combined with ATR) is recovered. The sample is placed in direct contact with the transmission crystal for ATR, revealing the presence of an IR spectrum compatible with the LPA (FIG. 6)

Figure 7:
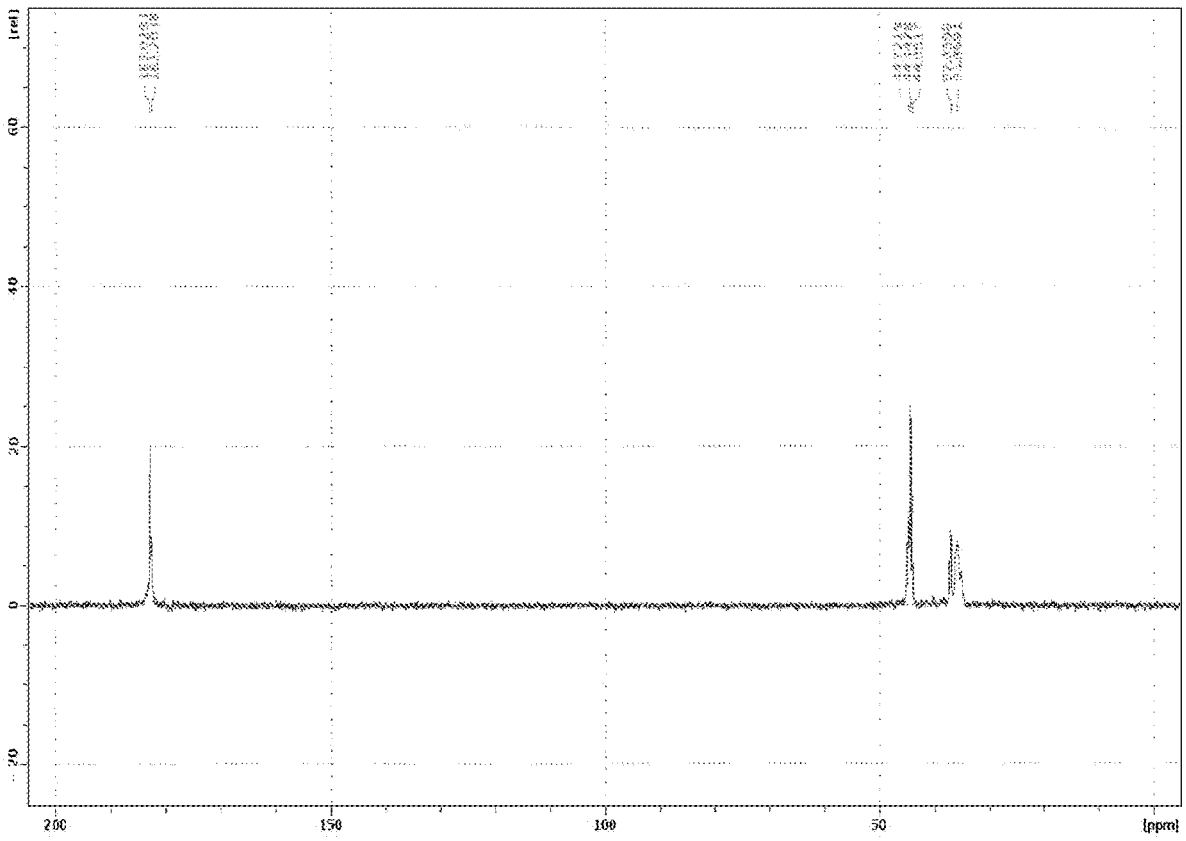
FIG. 7 shows the $^{13}$C-NMR spectrum conducted on a sample of liquid fraction derived from the method described, performed in deuterated water with a Bruker Avance 300 MHz spectrometer. The signal at about 84 ppm typical of the C carbon-CH$_2$— of the cross-linkers bearing alpha heteroatoms such as oxygen and/or nitrogen (—OCH$_2$—, —NHCH$_2$NH—, etc.) is absent, in turn bound to carbonyl groups C=O.

Dissolved in deuterated water, the dry compound was also analyzed by carbon nuclear magnetic resonance spectrometry $^{13}$C-NMR, revealing the absence of the signal at about 84 ppm, characteristic of the intramolecular cross-links of the SAP (Liu, Z. S., Rempel, G. L., Preparation of SAP by cross-linking Acrylic Acid and Acrylamide Copolymers, Appl Polym Sci 64:1345-1353, 1997) (FIG. 7).

The cellulose fraction separated from the liquid fraction and subjected to two washes with water includes a quantity of SAP less than 1% (analysis conducted in FTIR spectrophotometry combined with ATR). The solid sample is placed in direct contact with the transmission crystal for ATR, allowing the recording of the typical IR spectra of the cellulose.

Therefore almost all the SAP pass into the liquid fraction separated from the suspension, after at least two washing steps of the solid fraction.

Chemical analyzes confirm that the cellulose-based fraction is also compliant with the provisions of DECREE May 15 2019, no. 62-Regulation governing the termination of the qualification of waste from absorbent products for the person, pursuant to Article 184, paragraph 2, of Legislative Decree 3 Apr. 2006, no. 152.

Plastic (Particles Smaller than 3 cm Comprising SAP).

The plastic fraction was placed in a 1500 liter cylindrical stainless steel adiabatic reactor, which was thermostatable through heat exchange to be carried out or through the circulation of a heat transfer fluid in a coil, or through ohmic heating achieved through electrical resistances. The reactor used has a rod with fixed blades for mechanical stirring. A total of 442 liters of a commercial 30% hydrogen peroxide solution in water v/V, density 1.11 kg/L (300% with respect to the dry amount) were fed into the reactor with another 550 L of water (final oxidant concentration about 15% in weight compared to water), and heated to a temperature of 70° C. A total of 50 kg of wet plastic at 2% and with a temperature of about 20° C. was transferred to the reactor and placed in the bath. A disc-headed piston with 1 cm diameter holes, operated by a hydraulic pump, closes the head of the cylindrical reactor, exerting a pressure of 6 N/cm². The piston stroke is stopped when the liquid level emerges beyond the surface of the disc by means of a level sensor. The stirring of the blade rod is activated and an additional overheating is carried out up to 75° C., maintained for 20 minutes. After this period of time, the material is completely compressed by exerting a pressure of 16 N/cm² on the material, to allow the solution to rise above the perforated head of the piston. An outflow valve allows collection of the waste solution. One subsequent cycle, each with 75 L, which can be carried out with water only and in the cold, allows the recovery of any traces of residual LPA from the first stage of the process.

The separated plastic fraction, before the treatment by immersion, has a purity percentage of 85%, evaluated by FTIR spectrophotometry combined with the method for extracting the polyolefin fraction soluble in hot xylene (methods ASTM D5492-ISO 16152:2005 Plastics Determination of xylene-soluble matter in polypropylene-UNIEN ISO 6427:2013, Plastics: Determination of matter extractable by organic solvents).

The aqueous fraction recovered downstream of a wash was dried and analyzed by infrared spectrophotometry (FTIR combined with ATR), revealing the presence of an IR spectrum compatible with LPA, and by analysis with $^{13}$C-NMR, revealing the absence of the signal at about 84 ppm, characteristic of the intramolecular cross-links of the SAP.

The plastic fraction separated from the liquid fraction and washed with water comprises a quantity of SAP less than 1%. The solid sample is placed in direct contact with the transmission crystal for ATR, allowing the recording of the typical IR spectra of the plastic components, essentially based on polypropylene and polyethylene.

Therefore, almost all of the SAP is separated from the solid fraction to the liquid fraction.

FTIR spectrophotometric analysis combined with ATR reveals the presence of the cellulosic component as the only residual contamination of the plastic fraction. Known methods of extraction in the supercritical phase or, for example, of enzymatic hydrolysis, or by physical separation could allow removal of even the slightest contamination caused by cellulose residues from the plastic fraction.

Chemical analyzes confirm that the plastic-based fraction is also compliant with the provisions of DECREE May 15, 2019, no. 62-Regulation governing the termination of the qualification of waste from absorbent products for the person, pursuant to Article 184, paragraph 2, of Legislative Decree 3 Apr. 2006, no. 152.

Of course, without prejudice to the principle of the invention, the details of construction and the embodiments may be widely varied, without thereby departing from the scope of the invention as defined by the claims that follow.

The invention claimed is:

1. A method for separating a fraction of super-absorbent polymers (SAP) from post-consumer absorbent sanitary products, said post-consumer absorbent sanitary products further comprising at least one cellulose fraction and one plastic fraction, the method comprising the steps of:

sterilizing post-consumer absorbent sanitary products, treating said post-consumer absorbent sanitary products by immersion in a bath with an aqueous solution containing at least one oxidizing compound to cleave cross-links and solubilize the SAP contained in said post-consumer absorbent sanitary products, and obtaining a suspension comprising i) a solid fraction and ii) a liquid fraction, said liquid fraction comprising linear polyacrylate derived from the cross-link cleavage and solubilization of the SAP;

wherein said step for cleaving the cross-links and solubilizing the SAP is carried out after the sterilization step, by immersion in the bath with said aqueous solution of said sterilized post-consumer absorbent sanitary products, to obtain said suspension, wherein said solid fraction comprises the at least one cellulose fraction and the plastic fraction.

2. The method according to claim 1, wherein said sterilizing step is carried out by heating said post-consumer absorbent sanitary products at a temperature between 120° C. and 140° C. and at a pressure between 1 bar and 3.6 bar.

3. The method according to claim 1, wherein said at least one oxidizing compound is selected from the group consisting of sodium persulfate, potassium persulfate, ammonium persulfate, potassium monopersulfate, and hydrogen peroxide.

4. The method according to claim 1, wherein the method also comprises the steps of:

shredding said sterilized post-consumer absorbent sanitary products and obtaining sterilized and shredded absorbent sanitary products having a particle size less than 1 cm.

5. The method according to claim 4, wherein the method also comprises the step of drying said shredded post-consumer absorbent sanitary products and obtaining shredded and dried post-consumer absorbent sanitary products.

6. The method according to claim 4, wherein said step for cleaving the cross-links and solubilizing the SAP is carried out after the shredding step.

7. The method according to claim 6, wherein a ratio between a volume of said aqueous solution containing at least one oxidizing compound and the weight of said sterilized post-consumer absorbent sanitary products is comprised between 5 l/kg and 8 l/kg.

8. The method according to claim 1, wherein said step of treating said sterilized post-consumer absorbent sanitary products by immersion is carried out in the bath with the aqueous solution containing at least one oxidizing compound in an amount comprised between 10% and 50% (weight/weight).

9. The method according to claim 1, wherein said step of treating said post-consumer absorbent sanitary products by immersion is carried out at a temperature comprised between 65° C. and 100° C.

10. The method according to claim 1, wherein the method also comprises a step of separating said solid fraction from said liquid fraction contained in said suspension.

11. The method according to claim 10, wherein the method also comprises a step of purifying said liquid fraction containing linear polyacrylate.

* * * * *